US012527892B2

(12) United States Patent
Lay et al.

(10) Patent No.: US 12,527,892 B2
(45) Date of Patent: Jan. 20, 2026

(54) SELECTIVELY CONFIGURABLE WOUND DRESSING

(71) Applicant: ConvaTec Limited, Deeside (GB)

(72) Inventors: Amelia Lay, Deeside (GB); Andrew Peers, Deeside (GB); Duncan Gilding, Deeside (GB); Lucy Ballamy, Deeside (GB); Sally Leyland, Deeside (GB)

(73) Assignee: CONVATEC LIMITED, Flintshire (GB)

( * ) Notice: Subject to any disclaimer, the term of this patent is extended or adjusted under 35 U.S.C. 154(b) by 599 days.

(21) Appl. No.: 17/871,656

(22) Filed: Jul. 22, 2022

(65) Prior Publication Data

US 2023/0024230 A1 Jan. 26, 2023

Related U.S. Application Data

(63) Continuation of application No. PCT/GB2022/051919, filed on Jul. 22, 2022.

(30) Foreign Application Priority Data

Jul. 23, 2021 (GB) ..................................... 2110648

(51) Int. Cl.
*A61L 15/16* (2006.01)
*A61F 13/00* (2024.01)
(Continued)

(52) U.S. Cl.
CPC ........ *A61L 15/16* (2013.01); *A61F 13/00063* (2013.01); *A61F 13/05* (2024.01); *A61M 1/90* (2021.05)

(58) Field of Classification Search
CPC ................ A61F 13/00; A61F 13/00008; A61F 13/00021; A61F 13/00089; A61F 13/02; A61F 13/023; A61F 13/0233; A61F 13/0243; A61F 13/0246; A61F 13/0253; A61F 13/0266; A61F 2013/00604; A61F 5/01; A61M 1/87; A61M 1/90;
(Continued)

(56) References Cited

U.S. PATENT DOCUMENTS 11,717,447 B2 8/2023 Brownhill et al.
11,730,631 B2 8/2023 Rehbein et al.
(Continued)

FOREIGN PATENT DOCUMENTS

EP 2604299 A1 6/2013
EP 4326359 10/2022
(Continued)

OTHER PUBLICATIONS

UKIPO Search Report of corresponding application GB2110648.9; Date: Apr. 28, 2022; pp. 2.

*Primary Examiner* — Alireza Nia
*Assistant Examiner* — Andrew Jun-Wai Mok
(74) *Attorney, Agent, or Firm* — TAFT STETTINIUS HOLLISTER LLP; Ryan O. White; Derek B. Lavender

(57) ABSTRACT

A wound dressing is selectively configurable for use in a pressure gradient wound therapy system and for use without a pressure gradient wound therapy system. The wound dressing can include a covering layer, an aperture and a microbial barrier. The microbial barrier can be arranged to cover the aperture.

10 Claims, 6 Drawing Sheets

(51) Int. Cl.
*A61F 13/05* (2024.01)
*A61M 1/00* (2006.01)

(58) Field of Classification Search
CPC ........ A61M 1/91; A61M 1/912; A61M 1/915; A61M 1/916; A61M 1/917; A61M 1/96; A61M 1/962; A61M 1/98; A61M 25/02; A61M 2025/0213; A61M 2025/0273
See application file for complete search history.

(56) References Cited

U.S. PATENT DOCUMENTS

| | | | | |
|---|---|---|---|---|
| 11,730,854 | B2 | 8/2023 | Dagger et al. | |
| 11,730,874 | B2 | 8/2023 | Weston | |
| 11,730,876 | B2 | 8/2023 | Phillips et al. | |
| 11,737,925 | B2 | 8/2023 | Haggstrom et al. | |
| 11,744,740 | B2 | 9/2023 | Locke | |
| 11,744,741 | B2 | 9/2023 | Weston | |
| 11,752,253 | B2 | 9/2023 | Kharkar et al. | |
| 11,766,363 | B2 | 9/2023 | Locke et al. | |
| 11,791,030 | B2 | 10/2023 | Hunt et al. | |
| 11,793,923 | B2 | 10/2023 | Coulthard et al. | |
| 11,801,164 | B2 | 10/2023 | Hartwell et al. | |
| 11,806,215 | B2 | 11/2023 | Lin | |
| 11,806,217 | B2 | 11/2023 | Wheldrake | |
| 11,813,394 | B2 | 11/2023 | Joshi et al. | |
| 11,833,290 | B2 | 12/2023 | Locke et al. | |
| 11,839,527 | B2 | 12/2023 | Johnson et al. | |
| 11,850,121 | B2 | 12/2023 | Rapp | |
| 11,850,124 | B2 | 12/2023 | Osborne et al. | |
| 11,850,348 | B2 | 12/2023 | Weston et al. | |
| 11,857,746 | B2 | 1/2024 | Blott et al. | |
| 11,864,980 | B2 | 1/2024 | Locke et al. | |
| 11,877,911 | B2 | 1/2024 | Locke et al. | |
| 11,878,106 | B2 | 1/2024 | Ingram et al. | |
| 11,883,261 | B2 | 1/2024 | Coulthard et al. | |
| 11,883,578 | B2 | 1/2024 | Locke et al. | |
| 11,896,733 | B2 | 2/2024 | Zimnitsky et al. | |
| 11,896,754 | B2 | 2/2024 | Haggstrom et al. | |
| 11,903,798 | B2 | 2/2024 | Askem et al. | |
| 11,911,556 | B2 | 2/2024 | Mercer et al. | |
| 11,925,735 | B2 | 3/2024 | Gowans et al. | |
| 11,931,226 | B2 | 3/2024 | Collinson et al. | |
| 11,957,545 | B2 | 4/2024 | Hunt et al. | |
| 11,957,546 | B2 | 4/2024 | Coulthard et al. | |
| 11,963,850 | B2 | 4/2024 | Freedman et al. | |
| 11,964,095 | B2 | 4/2024 | Robinson et al. | |
| 11,969,319 | B2 | 4/2024 | Wilkes et al. | |
| 11,969,538 | B2 | 4/2024 | Quintanar | |
| 11,986,377 | B2 | 5/2024 | Clippert | |
| 11,992,601 | B2 | 5/2024 | Vess et al. | |
| 12,004,925 | B2 | 6/2024 | Hartwell | |
| 12,016,994 | B2 | 6/2024 | Hunt et al. | |
| 2008/0051688 | A1* | 2/2008 | Lowe | A61F 13/023 602/58 |
| 2011/0106030 | A1* | 5/2011 | Scholz | A61M 27/00 604/319 |
| 2011/0178481 | A1 | 7/2011 | Locke et al. | |
| 2015/0258259 | A1 | 9/2015 | Johannison | |
| 2018/0015197 | A1 | 1/2018 | Cotton | |
| 2018/0369462 | A1* | 12/2018 | Anderson | A61M 1/912 |
| 2020/0000985 | A1 | 1/2020 | Seddon et al. | |
| 2020/0121510 | A1 | 4/2020 | Hartwell et al. | |
| 2020/0337906 | A1 | 10/2020 | Long et al. | |
| 2023/0218445 | A1 | 7/2023 | Hunt et al. | |
| 2023/0233140 | A1 | 7/2023 | Hunt et al. | |
| 2023/0241301 | A1 | 8/2023 | Kelbie et al. | |
| 2023/0248314 | A1 | 8/2023 | Brownhill et al. | |
| 2023/0248896 | A1 | 8/2023 | Simmons et al. | |
| 2023/0263931 | A1 | 8/2023 | Lustiger et al. | |
| 2023/0270597 | A1 | 8/2023 | Locke et al. | |
| 2023/0277381 | A1 | 9/2023 | Cole et al. | |
| 2023/0277749 | A1 | 9/2023 | Collinson et al. | |
| 2023/0285198 | A1 | 9/2023 | Locke | |
| 2023/0301836 | A1 | 9/2023 | Locke | |
| 2023/0301838 | A1 | 9/2023 | Canner et al. | |
| 2023/0330321 | A1 | 10/2023 | Adie et al. | |
| 2023/0338650 | A1 | 10/2023 | Allen et al. | |
| 2023/0380754 | A1 | 11/2023 | Gowans et al. | |
| 2023/0381401 | A1 | 11/2023 | Locke | |
| 2023/0390481 | A1 | 12/2023 | Locke et al. | |
| 2023/0404813 | A1 | 12/2023 | Rehbein et al. | |
| 2023/0414824 | A1 | 12/2023 | Brewster et al. | |
| 2024/0000615 | A1 | 1/2024 | Locke | |
| 2024/0000618 | A1 | 1/2024 | Weston | |
| 2024/0009372 | A1 | 1/2024 | Braga et al. | |
| 2024/0016664 | A1 | 1/2024 | Ingram | |
| 2024/0033414 | A1 | 2/2024 | Howard et al. | |
| 2024/0050640 | A1 | 2/2024 | Locke et al. | |
| 2024/0074909 | A1 | 3/2024 | Rapp | |
| 2024/0074912 | A1 | 3/2024 | Simmons | |
| 2024/0091430 | A1 | 3/2024 | Hunt et al. | |
| 2024/0099894 | A1 | 3/2024 | Hartwell et al. | |
| 2024/0099897 | A1 | 3/2024 | Locke et al. | |
| 2024/0099898 | A1 | 3/2024 | Rice et al. | |
| 2024/0108515 | A1 | 4/2024 | Locke et al. | |
| 2024/0115789 | A1 | 4/2024 | Locke et al. | |
| 2024/0115792 | A1 | 4/2024 | Ingram et al. | |
| 2024/0130898 | A1 | 4/2024 | Long et al. | |
| 2024/0139035 | A1 | 5/2024 | Collinson et al. | |
| 2024/0148560 | A1 | 5/2024 | Coulthard et al. | |
| 2024/0148561 | A1 | 5/2024 | Rehbein et al. | |
| 2024/0156645 | A1 | 5/2024 | Braga et al. | |
| 2024/0181121 | A1 | 6/2024 | Hansson et al. | |
| 2024/0189492 | A1 | 6/2024 | Gowans et al. | |
| 2024/0197537 | A1 | 6/2024 | Coulthard et al. | |
| 2024/0197981 | A1 | 6/2024 | Kennedy et al. | |

FOREIGN PATENT DOCUMENTS

| | | | |
|---|---|---|---|
| EP | 4337277 | | 11/2022 |
| EP | 3139877 | B2 | 7/2023 |
| EP | 3740257 | B1 | 7/2023 |
| EP | 3551147 | B1 | 8/2023 |
| EP | 3634327 | B1 | 8/2023 |
| EP | 3827795 | B1 | 8/2023 |
| EP | 3990036 | B1 | 8/2023 |
| EP | 4221654 | A1 | 8/2023 |
| EP | 4221655 | A1 | 8/2023 |
| EP | 4223265 | A1 | 8/2023 |
| EP | 4226901 | A1 | 8/2023 |
| EP | 3181161 | B1 | 9/2023 |
| EP | 3700479 | B1 | 9/2023 |
| EP | 3700597 | B1 | 9/2023 |
| EP | 3876886 | B1 | 9/2023 |
| EP | 3880143 | B1 | 9/2023 |
| EP | 3990038 | B1 | 9/2023 |
| EP | 4237030 | A1 | 9/2023 |
| EP | 4238594 | A2 | 9/2023 |
| EP | 4247307 | A1 | 9/2023 |
| EP | 3096725 | B1 | 10/2023 |
| EP | 3402450 | B1 | 10/2023 |
| EP | 3058963 | B1 | 11/2023 |
| EP | 3595734 | B1 | 11/2023 |
| EP | 3622976 | B1 | 11/2023 |
| EP | 3876885 | B1 | 11/2023 |
| EP | 4294340 | A1 | 12/2023 |
| EP | 3452132 | B1 | 1/2024 |
| EP | 3769791 | B1 | 1/2024 |
| EP | 3659409 | B1 | 2/2024 |
| EP | 3986346 | B1 | 2/2024 |
| EP | 3651815 | B2 | 3/2024 |
| EP | 2990064 | B1 | 4/2024 |
| EP | 4346340 | A2 | 4/2024 |
| EP | 4353271 | A1 | 4/2024 |
| EP | 3292878 | B1 | 5/2024 |
| EP | 3700480 | B1 | 5/2024 |
| EP | 4178640 | B1 | 5/2024 |
| GB | 2611914 | B | 9/2023 |
| WO | 2011135286 | A1 | 11/2011 |
| WO | 202051548 | A1 | 3/2020 |
| WO | 2020146154 | A2 | 7/2020 |

(56) References Cited

FOREIGN PATENT DOCUMENTS

| | | | |
|---|---|---|---|
| WO | 2020229951 | A1 | 11/2020 |
| WO | 2021011181 | A1 | 1/2021 |

* cited by examiner

SELECTIVELY CONFIGURABLE WOUND DRESSING

CROSS REFERENCE TO RELATED DISCLOSURES

The present application is a continuation of PCT/GB2022/051919 filed on Jul. 22, 2022 and claims the benefit of priority application No. GB2110648.9 filed Jul. 23, 2021, the contents of which are hereby incorporated herein by reference in entirety.

TECHNICAL FIELD OF THE INVENTION

The present invention relates to a wound dressing and kit comprising such a wound dressing, and in particular to a wound dressing selectively configurable for use with a pressure gradient wound therapy apparatus or for use without a pressure gradient wound therapy apparatus.

BACKGROUND TO THE INVENTION

Health care professionals (HCPs) are required to evaluate and treat a variety of wounds with different requirements which can change as treatment progresses. Accordingly, HCPs keep stocks of different types of dressings for different requirements.

Pressure gradient wound therapy (positive or negative) is one known way of treating various wound types. Typically, this involves applying a pressure differential between a sealed region of a wound dressing and the surrounding environment to assist with healing the wound, e.g. through removal of oedema, increasing blood flow, mechanical contraction of the wound, increasing formation of granulation tissue and/or active removal of excess exudate from the wound. Wound therapy of this type is particularly effective for the treatment of open traumatic, non-traumatic and chronic wounds.

Amongst different types of dressings are those designed and intended for use as an advanced wound dressing to manage exudate and protect the wound. These can, for example, have a wound contact layer including gelling fibres, such as the Hydrofiber® technology included in Aquacel® surgical dressings available from ConvaTec Ltd of Deeside, UK, which transform into a gel on contact with wound fluid. (Such wound dressings are not intended for use with pressure gradient wound therapy, nor used for such applications in practice, owing to their construction.)

Other types of wound dressing are specially adapted to be used in conjunction with a pressure gradient wound therapy apparatus, e.g. with a negative pressure wound therapy (NPWT pump). In their original incarnation, NWPT systems had large, heavy (not portable/wearable) pump arrangements connected via tubing to the wound; at the wound, a reticulated open cell foam dressing is introduced into the wound and a separate adhesive drape is placed over the top. To connect the tubing to the wound in these large systems, a health care professional pinches the drape and foam beneath, and snips a hole through both drape and foam to form an aperture in the top for connection to the tubing. These systems and the two-part wound dressing (i.e. separate foam and drape) are still widely used in hospitals where professional staff are on-hand to set up to systems.

More recently, and especially in portable or wearable pressure gradient wound therapy systems intended for home-use, one-piece dressings have been introduced, in which an adhesive covering layer and dressing are integrated. An example of such a dressing is the Avelle® dressing available from ConvaTec Limited of Deeside UK. That dressing has a covering film layer with an adhesive border provided around its periphery to form a seal around the wound and a wound contact layer of stitch-bonded Hydrofiber® material. A foam pressure-distribution layer is provided between the covering layer and the wound contact layer (adjacent the covering layer) and additional layers of fenestrated Hydrofiber® layers are provided between the wound contact layer and the pressure-distribution layer. The covering layer is provided with an aperture, to allow connection of tubing from the negative pressure source and in this example, the dressing includes an "airway" extending from the aperture to a connector for connection to tubing through which negative pressure is provided.

Naturally, where a hospital or the like provides both "normal" wound dressings and those for use with pressure gradient wound therapy it needs to keep stocks of both, in various different sizes, which requires space, and lends complexity to the stock-ordering and stock selection process.

The present inventors have also identified that it would be beneficial to be able to provide a dressing that could be used for both pressure gradient wound therapy and "normal" treatment of wounds without a pressure gradient, in order that such treatment could be applied as and when required, and if no longer required, the dressings could still be used.

It is an aim of an embodiment or embodiments of the invention to overcome or at least partially mitigate one or more problems with the prior art and/or to provide an improved wound dressing.

SUMMARY OF THE INVENTION

According to a broad aspect of the invention there is provided a wound dressing selectively configurable for use in a pressure gradient wound therapy system and for use without a pressure gradient wound therapy system.

The wound dressing may comprise a wound contact layer; the wound contact layer may comprise a first surface for contacting a wound and an opposing second surface; the wound dressing may comprise a covering layer; the covering layer may have a first surface facing the wound contact layer; the first surface may define a cavity; the covering layer may comprise an opposing second surface; the covering layer may comprise an aperture; the aperture may be configured to provide fluid communication between the wound dressing cavity and a environment external to the dressing; the aperture may allow for use of the wound dressing with a pressure gradient would therapy system; the wound dressing may comprise a microbial barrier covering the aperture; the microbial barrier may allow for use of the wound dressing without a pressure gradient wound therapy system.

According to an aspect of the invention there is provided a wound dressing selectively configurable for use in a pressure gradient wound therapy system and for use without a pressure gradient wound therapy system; the wound dressing comprising a wound contact layer having a first surface for contacting a wound and an opposing second surface; and a covering layer having a first surface facing the wound contact layer and defining a wound dressing cavity, and an opposing second surface; the covering layer further comprising an aperture configured to provide fluid communication between the wound dressing cavity and an environment external to the dressing for use with a pressure gradient wound therapy system; wherein the wound dressing comprises a microbial barrier covering the aperture for use of the wound dressing without a pressure gradient wound therapy system.

Advantageously such a wound dressing can be used either with a pressure gradient wound therapy system, or without. Thus, stock-keeping is simplified. Moreover, if, during “normal” treatment without pressure gradient it is determined that it would be beneficial for pressure gradient wound therapy to be used, such a system could be added, by configuring the wound dressing accordingly (i.e. by applying a port about the aperture; optionally removing or piercing the microbial barrier) and attaching a source of non-atmospheric pressure (e.g. tubing from a NWPT pump). Notably, this could be done without the need for an additional dressing change, thus reducing the risk of wound infection. Similarly, if a wound is being treated with a pressure gradient, e.g. NWPT and the amount of exudate produced is reduced, so that NWPT is no longer required, a patient would be able to use up the stock of dressings without the NWPT system, by configuring them for use without the system (i.e. by maintaining the microbial barrier).

When used herein and throughout the specification the term “pressure gradient wound therapy apparatus” is intended to cover a wound therapy apparatus wherein a pressure differential (either positive or negative) is applied between a sealed region of the wound dressing and the surrounding environment.

As used herein, negative pressure wound therapy is a therapeutic technique using a suction dressing to remove excess exudation and promote healing in acute or chronic wounds. A vacuum of −50 to −200 mm Hg, or −75 to −150 mm Hg may be applied with typical negative pressure of −80 to −130 mm Hg, −100 to −130 mm Hg, or often about −125 mm Hg being applied to a wound.

For positive pressure wound therapy, a net positive pressure is applied to the wound, which may include providing simultaneous aspiration and irrigation of the wound. Positive pressure wound therapy may be carried out at a positive pressure of up to 50% atm., typically at a low positive pressure of up to 20% atm., more usually up to 10% atm. at the wound. Positive pressure wound therapy is known and referred to in US20180140755.

Optional features set out below may apply to any aspect of the invention.

The microbial barrier may be a layer. The microbial barrier may be a layer arranged on the first surface of the covering layer. The microbial barrier may be a layer arranged on the second surface of the covering layer. The microbial layer may be a layer arranged in the aperture, i.e. in the plane of the covering layer. The microbial barrier may comprise a film. The microbial barrier may comprise a foil. The microbial barrier may be fixedly attached to the covering layer. The microbial barrier may be releasably attached to the covering layer.

The microbial barrier may be a releasable layer. The releasable layer may be a film or foil. The microbial barrier may comprise a flap. The flap may be releasably adhered to the second surface of the covering layer. The releasable adhesive may be applied to the second surface of the covering layer. The flap may comprise a covering portion, covering the aperture. The flap may comprise a release tab. The covering portion may be releasably adhered to the covering layer. The release tab may be un-adhered to the covering layer. The release tab may be arranged on one edge of the covering portion. The release tab may be configured to be pulled by a user to expose the aperture. The covering portion may be rectangular. The release tab may be triangular, tapering away from the covering portion. The releasable adhesive may be configured to remain on the covering layer when the release layer is removed. The releasable adhesive may thus be configured to adhere to a port once the aperture is exposed.

As such, an aspect of the present disclosure provides a wound dressing selectively configurable for use in a pressure gradient wound therapy system and for use without a pressure gradient wound therapy system; the wound dressing comprising a wound contact layer having a first surface for contacting a wound and an opposing second surface; and a covering layer having a first surface facing the wound contact layer and defining a wound dressing cavity, and an opposing second surface; the covering layer further comprising an aperture configured to provide fluid communication between the wound dressing cavity and an environment external to the dressing for use with a pressure gradient wound therapy system; wherein the wound dressing comprises a microbial barrier covering the aperture for use of the wound dressing without a pressure gradient wound therapy system and wherein the microbial barrier comprises a releasable layer, wherein the releasable layer is a flap comprising a covering portion and a release tab; wherein the covering portion is releasably adhered to the covering layer with a releasable adhesive and the release tab is not adhered to the covering layer.

The covering layer may comprise a plurality of perforations. The perforations may define a perimeter of the aperture. The section of the covering layer within the perforations may be a removable portion or “chad”. The microbial barrier may be arranged to cover the perforations. The removeable portion or “chad” of the covering layer may be configured to tear away from the remainder of the covering layer along the plurality of perforations. The removeable portion may be adhered to the releasable layer, for example to the covering portion of the flap. Thus, as the flap is removed, the removeable portion may be removed to expose the aperture.

The microbial barrier may comprise a filter. The filter may be made of PTFE. The filter may be made of Polyester Sulfone. The filter may be a PTFE membrane filter, or a slimline cartridge. The filter may be liquid impermeable. The filter may be gas permeable. The filter may be impermeable to bacteria and/or viruses. The filter may be permeable to water vapor.

The microbial barrier may be a membrane. The membrane may be permeable to gas. The membrane may be permeable to water vapor. The membrane may be impermeable to bacteria and/or viruses. The membrane may be impermeable to liquids. The microbial barrier may comprise a semi-permeable membrane.

The microbial barrier may comprise an occlusive material. The occlusive material may be a foil or film layer. The occlusive material may be a Polyethylene film, or the occlusive material may be a PET film, or the occlusive material may be an aluminium foil. The occlusive material may be impermeable to liquid, impermeable to moisture vapour and impermeable to gas.

The dressing may comprise a port or a part thereof. The port or part thereof may surround the aperture. The port may be part of a two-part port. The dressing may comprise a base plate of a two-part port. The port may be configured to receive a connection to a source of non-atmospheric pressure. The base plate may be configured to connect to a second port component.

When configured for use without the pressure gradient wound therapy system the wound dressing may not comprise a port. When configured for use without the pressure gradient wound therapy system the wound dressing may not comprise a base plate of a two-part port.

The aperture is preferably located out of alignment (i.e. vertical alignment in use) with the centre of the dressing. For example it may be located towards the periphery of the covering layer and/or a pressure distribution layer (or the wound when in use). This assists in the spread of exudate across the full extent of the pressure distribution layer (and across an absorbent layer where an absorbent layer is provided).

A pressure distribution layer may be provided adjacent to the cover layer. The pressure distribution layer may be provided in, e.g. contained in, the cavity. The pressure distribution layer may be gas and liquid permeable and particularly moisture vapour permeable. The pressure distribution layer serves to aid access of exudate to a greater area of the absorbent layer by allowing it to spread under the distribution layer. The pressure distribution layer also serves to even out the negative pressure applied to the wound over the whole dressing (when used for NWPT). The pressure distribution layer is preferably configured to distribute exudate and negative pressure over the dressing. The pressure distribution layer is preferably a foam layer such as a polyester foam of the type XD4200AS manufactured by Caligen or another suitable reticulated foam.

An adhesive layer may be provided so as to form an adhesive border. The adhesive layer may be provided on the underside of the covering layer. The adhesive border may be provided at the periphery of the dressing arranged to adhere the dressing to the skin surrounding the wound to form a fluid tight seal. The adhesive layer may be provided with perforations to assist transport of exudate and fluid through the dressing. The adhesive layer may also be applied to any of the other layers to provide an island configuration.

The aperture may be located in a region of the covering layer within that defined by the adhesive border. For example it may be located towards the periphery of the region of the covering layer inwards of the adhesive border. In the configuration for use without a pressure gradient wound therapy system the region of the covering layer within that defined by the adhesive border may be closed by the microbial barrier. This restricts/prevents microbes, bacteria or the like from entering the wound dressing and hence from entering the wound. In the configuration for use with a pressure gradient wound therapy system the region of the covering layer within the adhesive border may be interrupted by the opening, the opening being the exposed aperture in the covering later for connection to a source of non-atmospheric pressure.

The aperture may be configured to provide fluid communication between the wound dressing cavity and a source of non-atmospheric pressure.

The wound dressing may include a dressing body comprising an absorbent material for contacting the wound, which may be positioned in contact with a wound, in use. The dressing body may be formed from one of more layers. The dressing body may be configured to absorb exudate from the wound, aided by the action of a connected pump assembly. The dressing body may comprise an absorbent foam material, for example a layer of absorbent foam material. The foam material may comprise a superabsorbent material, for example a superabsorbent foam material. The dressing body may be formed of a hydrocolloid material which may gel in the presence of an exudate. The hydrocolloid material may comprise a layer or multiple layers of gelling fibres and absorbent materials. The covering layer may be constructed of a thin film layer (e.g. a polyurethane) enabling moisture vapour to exit the dressing at an increased rate. This combination is particularly suitable for allowing the wound therapy apparatus to manage fluid without the need of a canister. This may be referred to as a "canister-less" or "canister-free" system. In a variant, the wound dressing may be operable to be fluidly connected to a canister into which exudate removed from the wound may be withdrawn. The adhesive border may define an interior region of the wound dressing. The dressing body may be provided in the cavity of the wound dressing.

The wound dressing may comprise a release layer, the release layer being removable to reveal the adhesive border.

The wound dressing may have a thickness between 1 mm to 20 mm, or 2 mm to 10 mm, or 3 mm to 7 mm, for example.

The pressure distribution layer may be a foam layer. The wound dressing may comprise the outer covering layer, the pressure distribution layer, one or more absorbent layer(s) and a silicone gel wound contact layer. The wound dressing may comprise an outer covering layer and one or more absorbent layer(s) in combination with a gel-forming fibre. The gel-forming fibre typically is in direct contact with the wound, and thus no additional wound contact layer is required i.e., a silicone gel wound contact layer does not require a silicone gel layer.

Gel-forming fibres include hygroscopic fibres which upon the uptake of wound exudate become moist slippery or gelatinous. The gel forming fibres can be of the type which retain their structural integrity on absorption of exudate or can be of the type which lose their fibrous form and become an amorphous or structureless gel. The gel forming fibres are preferably sodium carboxymethylcellulose fibres, chemically modified cellulosic fibres, alkyl sulphonate modified cellulosic fibres such as those described in WO2012/061225, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit. The gel forming fibres preferably have an absorbency of at least 2 grams 0.9% saline solution per gram of fibre (as measured by the free swell method).

The gel forming fibres are preferably chemically modified cellulosic fibres in the form of a fabric and in particular carboxymethylated cellulose fibres as described in PCT WO00/01425 to Azko Nobel UK Ltd, and can be provided by a layer of gel forming fibres preferably located in a port of the cover layer or as a layer of fibres in a conduit of the wound dressing. When present in the conduit, the layer of fibres can also serve to keep the conduit open to the passage of fluid in the event that the conduit is kinked or otherwise restricted by being lain on or leaned on by the user. The carboxymethylated cellulosic fabrics preferably have a degree of substitution between 0.12 to 0.35 as measured by IR spectroscopy (as defined in WO00/01425) more preferably a degree of substitution of between 0.20 and 0.30 and are made by carboxymethylating a woven or non-woven cellulosic fabric such that the absorbency is increased. Particular preferred fabrics have an absorbency of between 10 g/g of sodium/calcium chloride as defined above to 30 g/g of sodium/calcium chloride as measured by the method described in BS EN 13726-1 (2002) "Test methods for primary wound dressings", section 3.2 "Free swell absorptive capacity". Particularly preferred fabrics have an absorbency of 15 g/g to 25 g/g and most preferred of 15 g/g to 20 g/g of sodium/calcium chloride as measured by the method defined above.

The cellulosic fabric preferably consists solely of cellulosic fibre but may contain a proportion of non-cellulosic textile fibre or gel forming fibre. The cellulosic fibre is of known kind and may comprise continuous filament yarn and/or staple fibre. The carboxymethylation is generally performed by contacting the fabric with an alkali and a carboxymethylating agent such a chloracetic acid in an aqueous system. The fabric is preferably of a non-woven type to reduce shedding in the wound on cutting the dressing. Preferably the fabric is hydroentangled and thus comprises a series of apertures on a microscopic scale.

Where present, the absorbent layer of the wound dressing is capable of absorbing exudate from the wound and allowing the passage of fluid through it. The absorbent layer can comprise any absorbent capable of absorbing exudate while allowing the passage of fluid through it, such as a foam, sponge or fibre-based material, preferably the absorbent layer is provided by gel forming fibres of the same type or of a different type as those discussed above. The gel-forming fibres are hygroscopic fibres which upon the uptake of wound exudate become moist slippery or gelatinous and thus reduce the tendency for the surrounding fibres to adhere to the wound. The gel forming fibres are preferably spun sodium carboxymethylcellulose fibres, chemically modified cellulosic fibres, alkyl sulphonate modified cellulosic fibres such as those described in WO2012/061225, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit and more preferably are lightly substituted so that the absorbency of the fibres is limited. The gel forming fibres preferably have an absorbency of at least 2 grams 0.9% saline solution per gram of fibre (as measured by the method described above) but less than 30 grams 0.9% saline solution per gram of fibre. The gel forming fibres are preferably carboxymethylated cellulose fibres as described in PCT WO00/01425 to Azko Nobel UK Ltd which describes lightly carboxymethylated cellulose fabrics. The gel forming fibres are preferably lightly carboxymethylated in order to reduce the tendency of the absorbent layer to gel block and block the pathway for fluid from the wound, e.g. through the absorbent layer, the port and to a distal end of the conduit.

Preferably an absorbent layer is provided with fenestrations to aid the application of negative pressure to the wound and maintain the pathway for fluid from the wound, through the absorbent layer. Typically, however, fenestrations are only provided in internal absorbent layers.

Although the absorbent layer can be in direct contact with the wound, preferably the dressing comprises a dedicated and different wound contact layer, positioned between the wound and the absorbent layer(s). The wound contact layer may be capable of absorbing exudate from the wound and transmitting it to the absorbent layer. Thus, there may be provided "internal" absorbent layers as defined above, preferably including fenestrations and an external absorbent layer, which forms the wound contact layer. Like the internal absorbent layer, the wound contact layer may be capable of allowing the passage of fluid through it so that pressure (either positive or negative) may applied to the wound and the pathway for fluid/exudate from the wound to the distal end of the conduit may be maintained.

The wound contact layer may include gel-forming fibres (e.g. of the type discussed herein), or a silicone gel, for example.

Preferably the wound contact layer comprises gel-forming fibres. The gel-forming fibres may be the same or a similar type to those comprising the absorbent layer but the wound contact layer may be strengthened to increase its integrity and that of the dressing. For example, the wound contact layer may be of the type described in EP 1904011 and comprise gel-forming fibres in the form of a mat with lines of longitudinal stitching made of cellulose or nylon or polyolefin yarn to increase the integrity of the layer. Preferably the wound contact layer is porous to maintain the pathway for fluid/exudate from the wound to the distal end of the conduit.

Preferably the one or more absorbent layer(s) comprise an internal absorbent layer provided with fenestrations to aid the application of negative pressure to the wound and maintain the pathway for fluid from the wound, through the internal absorbent layer and a wound contact layer comprising gel-forming fibres is also provided.

The (outer) covering layer of the dressing is provided as a bacterial and viral barrier layer which preferably resists the ingress of liquid and air but allows moisture vapour transmission. In this way the cover layer enhances the overall fluid handling capacity of the dressing by allowing for the escape of moisture vapour through the cover while enabling the application of pressure (either positive or negative) to the wound. The outer cover layer is for instance a layer having a MVTR of at least 10,000 g $m^{-2}$ per 24 hours or in the range of from 10,000 $gm^{-2}$ to 50,000 g $m^{-2}$ per 24 hours measured by the method described in BS EN 13726-2 2002 "Test methods for primary wound dressings Part 2 Moisture vapour transmission rate of permeable film dressings". The cover layer may be in the form of a film of polyurethane, for example Epurex 912 T/129 manufactured by Covestro or Inspire 2350 manufactured by Coveris or Medifilm 426 manufactured by Mylan.

The wound dressing preferably is a one-piece dressing. That is to say, the covering layer and the body of the wound dressing are provided as an integral item, preferably including an adhesive layer and preferably including a removable release layer.

According to another broad aspect of the invention, there is provided a kit of parts including a selectively configurable wound dressing, the wound dressing being configurable for use in a pressure gradient wound therapy system and without a pressure gradient wound therapy system; the kit further comprising at least one of: (a) packaging indicating that the wound dressing is selectively configurable for use in a pressure gradient wound therapy system and without a pressure gradient wound therapy system; (b) instructions instructing a user as to how to configure the wound dressing for use in a pressure gradient wound therapy system and for use without a pressure gradient wound therapy system; (c) a source of non-atmospheric pressure; (d) a port for connection to the covering layer of the wound dressing to connect the wound dressing to a source of non-atmospheric pressure; or (e) tubing for connection between a wound dressing and a source of non-atmospheric pressure.

The wound dressing may comprise a wound contact layer and a covering layer, the covering layer having a first surface facing the wound contact layer and defining a wound dressing cavity, and a second surface; wherein the covering layer comprises an aperture, the aperture in a suitable, or more preferably an optimal, position in the covering layer to provide fluid communication between the wound dressing cavity and a source of non-atmospheric pressure; wherein the wound dressing comprises a microbial barrier covering the aperture for use of the wound dressing without a pressure gradient wound therapy system.

According to another aspect of the invention, there is provided a kit of parts including a selectively configurable wound dressing, the wound dressing being configurable for use in a pressure gradient wound therapy system and without a pressure gradient wound therapy system; the kit further comprising at least one of: (a) packaging indicating that the wound dressing is selectively configurable for use in a pressure gradient wound therapy system and without a pressure gradient wound therapy system; (b) instructions instructing a user as to how to configure the wound dressing for use in a pressure gradient wound therapy system and for use without a pressure gradient wound therapy system; (c) a source of non-atmospheric pressure; (d) a port for connection to the covering layer of the wound dressing to connect the wound dressing to a source of non-atmospheric pressure; or (e) tubing for connection between a wound dressing and a source of non-atmospheric pressure; wherein the wound dressing comprises a wound contact layer and a covering layer, the covering layer having a first surface facing the wound contact layer and defining a wound dressing cavity, and a second surface; wherein the covering layer comprises an aperture, the aperture configured to provide fluid communication between the wound dressing cavity and an external environment (in particular a source of non-atmospheric pressure); wherein the wound dressing comprises a microbial barrier covering the aperture for use of the wound dressing without a pressure gradient wound therapy system.

As noted above, the optional features set out above are equally applicable to all aspects (or embodiments) of the invention. For example, the selectively configurable wound dressing of the aspects of the invention concerning kit may be the selectively configurable wound dressing of either of the aspects outlined above including any of the optional features set out.

In one embodiment there is provided a kit of parts including a selectively configurable wound dressing, the wound dressing being configurable for use in a pressure gradient wound therapy system and without a pressure gradient wound therapy system; the kit further comprising: (a) packaging indicating that the wound dressing is selectively configurable for use in a pressure gradient wound therapy system and without a pressure gradient wound therapy system; wherein the wound dressing comprises a wound contact layer and a covering layer, the covering layer having a first surface facing the wound contact layer and defining a wound dressing cavity, and a second surface; wherein the covering layer comprises an aperture, the aperture configured to provide fluid communication between the wound dressing cavity and an external environment (in particular a source of non-atmospheric pressure); wherein the wound dressing comprises a microbial barrier covering the aperture for use of the wound dressing without a pressure gradient wound therapy system.

In another embodiment there is provided a kit of parts including a selectively configurable wound dressing, the wound dressing being configurable for use in a pressure gradient wound therapy system and without a pressure gradient wound therapy system; the kit further comprising: (b) instructions instructing a user as to how to configure the wound dressing for use in a pressure gradient wound therapy system and for use without a pressure gradient wound therapy system; wherein the wound dressing comprises a wound contact layer and a covering layer, the covering layer having a first surface facing the wound contact layer and defining a wound dressing cavity, and a second surface; wherein the covering layer comprises an aperture, the aperture configured to provide fluid communication between the wound dressing cavity and an external environment (in particular a source of non-atmospheric pressure); wherein the wound dressing comprises a microbial barrier covering the aperture for use of the wound dressing without a pressure gradient wound therapy system.

In another embodiment, there is provided a kit of parts including a selectively configurable wound dressing, the wound dressing being configurable for use in a pressure gradient wound therapy system and without a pressure gradient wound therapy system; the kit further comprising: (c) a source of non-atmospheric pressure; wherein the wound dressing comprises a wound contact layer and a covering layer, the covering layer having a first surface facing the wound contact layer and defining a wound dressing cavity, and a second surface; wherein the covering layer comprises an aperture, the aperture configured to provide fluid communication between the wound dressing cavity and the source of non-atmospheric pressure; wherein the wound dressing comprises a microbial barrier covering the aperture for use of the wound dressing without a pressure gradient wound therapy system.

In another embodiment, there is provided a kit of parts including a selectively configurable wound dressing, the wound dressing being configurable for use in a pressure gradient wound therapy system and without a pressure gradient wound therapy system; the kit further comprising: (d) a port (or part thereof) for connection to the covering layer of the wound dressing to connect the wound dressing to a source of non-atmospheric pressure; wherein the wound dressing comprises a wound contact layer and a covering layer, the covering layer having a first surface facing the wound contact layer and defining a wound dressing cavity, and a second surface; wherein the covering layer comprises an aperture, the aperture configured to provide fluid communication between the wound dressing cavity and the source of non-atmospheric pressure; wherein the wound dressing comprises a microbial barrier covering the aperture for use of the wound dressing without a pressure gradient wound therapy system.

In another embodiment, there is provided a kit of parts including a selectively configurable wound dressing, the wound dressing being configurable for use in a pressure gradient wound therapy system and without a pressure gradient wound therapy system; the kit further comprising: (e) tubing for connection between a wound dressing and a source of non-atmospheric pressure; wherein the wound dressing comprises a wound contact layer and a covering layer, the covering layer having a first surface facing the wound contact layer and defining a wound dressing cavity, and a second surface; wherein the covering layer comprises an aperture, the aperture configured to provide fluid communication between the wound dressing cavity and the source of non-atmospheric pressure; wherein the wound dressing comprises a microbial barrier covering the aperture for use of the wound dressing without a pressure gradient wound therapy system.

Of course the kit may comprise various combinations of features a to e; for example the kit may comprise at least two features including a+b; the kit may comprise at least two features including a+c; the kit may comprise at least two features including a+d; the kit may comprise at least two features including a+e; the kit may comprise at least two features including b+c; the kit may comprise at least two features including b+d; the kit may comprise at least two features including b+e; the kit may comprise at least two features including c+d; the kit may comprise at least two features including c+e; or the kit may comprise at least two features including d+e. The kit may comprise at least three features including a+b+c; the kit may comprise at least three features including a+b+d; the kit may comprise at least three features including a+b+e; the kit may comprise at least three features including a+c+d; the kit may comprise at least three features including a+c+e; the kit may comprise at least three features including a+d+e; the kit may comprise at least three features including b+c+d; the kit may comprise at least three features including b+c+e; the kit may comprise at least three features including b+d+e; or the kit may comprise at least three features including c+d+e. The kit may comprise at least four features including a+b+c+d; the kit may comprise at least four features including a+b+c+e; or the kit may comprise at least four features including b+c+d+e. The kit may comprise all five features a+b+c+d+e.

One particular embodiment includes at least one item selected from a+b; one particular embodiment includes at least one item selected from a+c; one particular embodiment includes at least one item selected from a+d; one particular embodiment includes at least one item selected from a+e; one particular embodiment includes at least one item selected from b+c; one particular embodiment includes at least one item selected from b+d; one particular embodiment includes at least one item selected from b+e; one particular embodiment includes at least one item selected from c+d; one particular embodiment includes at least one item selected from c+e; one particular embodiment includes at least one item selected from d+e; one particular embodiment includes at least one item selected from a+b+c; one particular embodiment includes at least one item selected from a+b+d; one particular embodiment includes at least one item selected from a+b+e; one particular embodiment includes at least one item selected from a+c+d; one particular embodiment includes at least one item selected from a+c+e; one particular embodiment includes at least one item selected from a+d+e; one particular embodiment includes at least one item selected from b+c+d; one particular embodiment includes at least one item selected from b+c+e; one particular embodiment includes at least one item selected from b+d+e; one particular embodiment includes at least one item selected from c+d+e; one particular embodiment includes at least one item selected from a+b+c+d; one particular embodiment includes at least one item selected from a+b+c+e; one particular embodiment includes at least one item selected from b+c+d+e; one particular embodiment includes at least one item selected from a+b+c+d+e.

The packaging may for example be cardboard packaging. The packaging may comprise printed information indicating that the wound dressing is selectively configurable for use in a pressure gradient wound therapy system and without a pressure gradient wound therapy system. The packaging may be sterile; and/or at least part of the packaging, or a sub-package may be sterile.

The instructions instructing a user as to how to configure the wound dressing for use in a pressure gradient wound therapy system and for use without a pressure gradient wound therapy system may be printed on packaging. The instructions instructing a user as to how to configure the wound dressing for use in a pressure gradient wound therapy system and for use without a pressure gradient wound therapy system may be provided on an instruction sheet (which where the kit includes features a+b may be provided in the packaging).

The source of non-atmospheric pressure preferably a source of negative pressure. Alternatively it may be a source of positive pressure. The source of non-atmospheric pressure may be a pump.

The port for connection to the covering layer of the wound dressing to connect the wound dressing to a source of non-atmospheric pressure may be provided with an airway. The airway may be a transparent passageway securable to the outside of the cover layer at the proximal end of the conduit so as to surround the aperture in the cover layer from above. The port/airway may comprise a connector, at its distal end, for connecting the dressing to a source of pressure (either positive or negative), for example a pump. Preferably the connector is a Luer lock to facilitate secure connection to the pump and to maintain the pressure within the wound dressing while the pump is temporarily disconnected. The connector preferably comprises a one-way lock to assist in the maintenance of the applied pressure. To resist collapse, the airway may comprise an internal cylinder of nylon fibres to maintain openness of the airway to fluid.

The tubing for connection between a wound dressing and a source of non-atmospheric pressure may be transparent tubing. The tubing may be flexible. The tubing may be resilient. The tubing may be formed from a resilient flexible plastics material.

According to another aspect of the invention there is provided a pressure gradient wound therapy apparatus, comprising the kit of any preceding aspect of the invention.

In embodiments, the wound therapy apparatus comprises a negative pressure wound therapy apparatus. In other embodiments, the wound therapy apparatus comprises a positive pressure wound therapy apparatus.

In embodiments, the apparatus may comprise a canister and the wound dressing may be fluidly connected to the canister into which exudate removed from the wound may be withdrawn. In preferred embodiments, the wound dressing may be formed of a hydrocolloid material which may gel in the presence of an exudate and the apparatus may include no cannister. This may be referred to as a "canister-less" system.

The pump assembly may be fluidly connected to an interior region of the wound dressing, for introducing and/or removing gas from within the wound dressing to control the pressure therein.

According to a further broad aspect of the invention there is provided a method of configuring a selectively configurable wound dressing, the wound dressing being configurable for use in a pressure gradient wound therapy system and without a pressure gradient wound therapy system; the method comprising configuring the wound dressing for use with a pressure gradient wound therapy system by applying a source of non-atmospheric pressure to the aperture.

The wound dressing may comprise a covering layer, which may comprise an aperture; and a microbial barrier; the aperture may be configured to provide fluid communication between the pressure distribution layer and a source of non-atmospheric pressure; the microbial barrier may cover the aperture; the method may comprise applying a port surrounding the aperture; the method may comprise removing (or partially removing) the microbial barrier.

According to an aspect of the invention there is provided a method of configuring a selectively configurable wound dressing, the wound dressing being configurable for use in a pressure gradient wound therapy system and without a pressure gradient wound therapy system; the wound dressing comprising a covering layer and a microbial barrier, the covering layer comprising an aperture to provide fluid communication between a wound dressing cavity and an environment external to the dressing; and the microbial barrier covering the aperture; the method comprising configuring the wound dressing for use with a pressure gradient wound therapy system by applying a source of non-atmospheric pressure to the aperture.

Of course, the wound dressing of the method aspects may be the wound dressing of the aspects of the wound dressing outlined above. And again, of course the wound dressing may comprise any optional feature described above.

The method may comprise breaking or removing the microbial barrier. The microbial barrier may be removed by pulling a tab provided on the microbial barrier. The microbial barrier may be broken by cutting through it.

The covering layer may comprise perforations defining a perimeter of the aperture. The method may comprise removing the section of the covering layer within the perforations.

The wound dressing may comprise a releasable layer. The method may comprise removing the releasable layer to remove the section of the covering layer within the perforations.

The wound dressing may comprise a release layer on the underside of the dressing. The method may comprise cutting the aperture, then removing the release layer, then applying the dressing to a wound.

The method may be a method of re-purposing a wound dressing that is provided on a wound and configured for use without a pressure gradient wound therapy system; the method comprising exposing an aperture in the wound dressing (in-situ, e.g. by removing a microbial barrier) in order to configure the wound dressing for use with a pressure gradient wound therapy system.

The method may comprise of re-purposing a wound dressing that is provided on a wound and configured for use without a pressure gradient wound therapy system (in-situ) by attaching a non-atmospheric pressure source to the wound dressing to apply non-atmospheric pressure through the aperture.

DETAILED DESCRIPTION OF THE INVENTION

In order that the invention may be more clearly understood one or more embodiments thereof will now be described, by way of example only, with reference to the accompanying drawings, of which:

Figure 1:
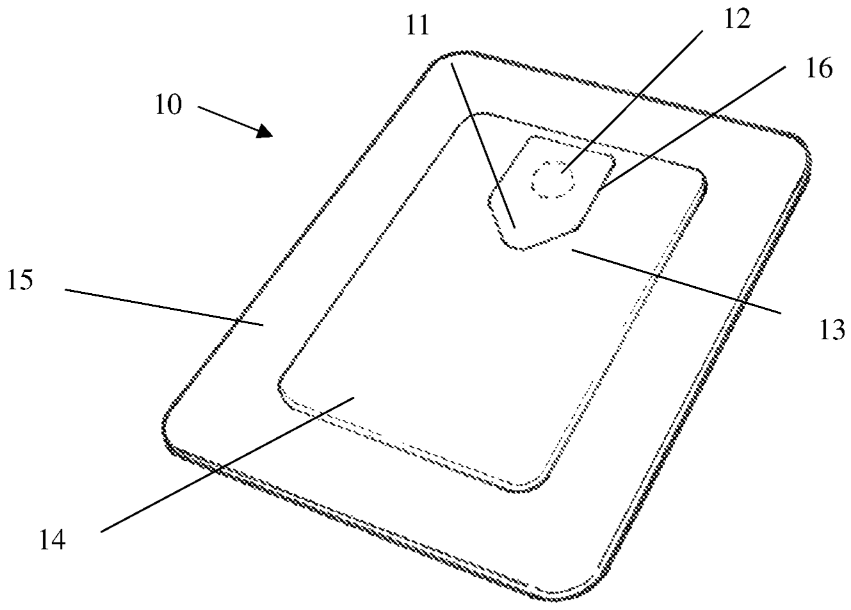
FIG. 1 is a schematic representation of an embodiment of a wound dressing configured for use without a wound therapy apparatus.

Embodiments disclosed herein relate to apparatus and methods of treating a wound both with and without reduced or positive pressure (typically negative pressure). Some embodiments including pump and wound dressing component. The wound dressings discussed are "one-piece" dressings incorporating both a covering layer and an absorbent body.

As disclosed herein the present invention may comprise a wound dressing; or a kit comprising the wound dressing and other apparatus for providing pressure gradient wound therapy to a wound.

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds (either as a result of surgery, trauma, stemiotomies, fasciotomies, or other conditions), dehisced wounds, acute wounds, chronic wounds, subacute and dehisced wounds, traumatic wounds (such as from orthopaedic trauma), flaps and skin grafts, lacerations, abrasions, contusions, burns, diabetic ulcers, pressure ulcers, stoma, surgical wounds, trauma and venous ulcers, broken bones or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

The technology disclosed can be used on an acute or chronic wound.

Wounds are believed to be more susceptible to infection under the following circumstances. If the wounds are chronic wounds, or if an object which caused the wound was dirty or contained bacteria, or from a bite, or contains remnant or a whole object that caused the wound, or a wound that is large or deep, or jagged edges to the wound, or elderly, or chronic because by their nature a wound site is open; and/or if the patient has: diabetes type 1 or type 2, is elderly, or has a compromised immune system.

Pressure gradient wound therapy may also be useful for treating second- and third-degree burns, as well as being useful for laparotomy surgery i.e., a large incision through an abdominal wall to gain access into the abdominal cavity.

Figure 2:
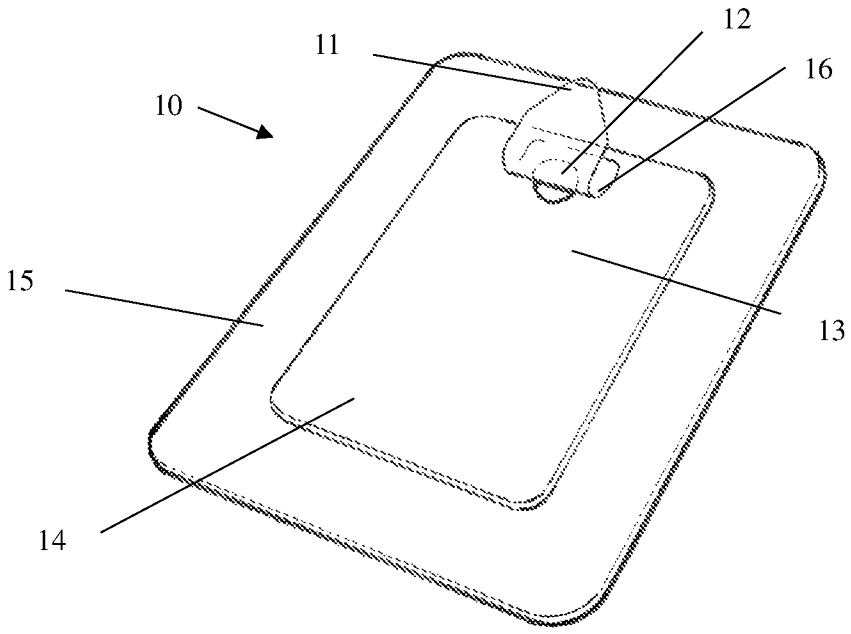
FIG. 2 is a schematic representation of the wound dressing of FIG. 1 configured for use with a wound therapy apparatus.

FIGS. 1 and 2 illustrate an embodiment of a wound dressing 10 in accordance with the invention in two different configurations.

In general, the invention relates to a wound dressing 10, which is selectively configurable for use without a pressure gradient wound therapy system or for use with a pressure gradient wound therapy system, e.g. negative pressure wound therapy.

As shown in FIG. 1, the wound dressing 10 includes an aperture 12 in a covering layer 13 of the dressing 10. The covering layer 13 has a raised central region 14, where it overlies a dressing body, which can include a pressure dispersion layer; an absorbent/superabsorbent layer/layers; and a wound-contact layer. The dressing 10 also has a border region 15, where it overlies an adhesive layer. A removable release layer (not shown) is provided on the underside.

The aperture 12 and covering layer 13 proximate to the aperture 12 are covered by a flap 16. The flap 16 of this embodiment is formed from a plastics film, such as polyethylene and releasably adhered to the covering layer 13 surrounding the aperture 12. In this particular embodiment, the adhesive that releasably adheres to the flap 16 is applied to, and adheres more strongly to the outside surface of the covering layer 13. The flap also has a tapered release tab 11 from one edge of the flap 16, the release tab 11 is not adhered to the covering layer.

As illustrated in FIG. 1, the wound dressing is configured for use without a pressure gradient wound therapy system. To use the wound dressing 10 without a pressure gradient wound therapy system, the release layer (not shown) on the underside is simply removed and the dressing applied in the same way as an ordinary wound dressing. It will be noted that when the flap 16 covers the aperture 12, it forms a microbial barrier, and as such, the entire raised central region 14 of the covering layer 13 is closed, so that the wound (within the region defined by the adhesive border) is in a sealed environment restricting/preventing bacteria/microbes entering the wound and causing infection.

FIG. 2 shows the wound dressing 10 of FIG. 1 configured for use with a pressure gradient wound therapy system. Here, a user has peeled back the flap 16, by pulling on the release tab 11, to expose the aperture 16 in the wound dressing 10 (so that the central region 14 is interrupted and no longer closed). With the wound dressing 10 now configured for use with a pressure gradient therapy system, a source of non-atmospheric, e.g. negative, pressure can be connected to the aperture 12 to aid the wound-healing process. Those skilled in the art will appreciate that the steps to configure the wound dressing 10 for use with a pressure gradient wound therapy system can be undertaken either prior to or after the wound dressing 10 has been applied to the wound (i.e. the wound dressing can be configured for use with a pressure gradient wound therapy system in-situ).

For example, a port (not shown in FIG. 1 or 2) can be adhered to the wound dressing 10, such that a conduit through the port is aligned with the aperture 16; the port can be connected via tubing (also not shown in FIGS. 1 and 2) to a pump (also not shown in FIGS. 1 and 2) producing negative pressure. Optionally, the releasable adhesive which held the flap 16 may also be used to adhere the port to the covering layer 13.

Optionally in this embodiment the space within the aperture 12 may not be empty when the wound dressing is configured for use without a pressure gradient wound therapy system. That is to say, the covering layer 13 may be perforated, with a plurality of perforations, arranged to define a perimeter of an aperture, but without the "chad" defined by the perforations removed. As such, when configuring the wound dressing for use with a pressure gradient wound therapy system, when the user peels back the flap 16 by pulling on the release tab 11, the chad, being adhered to the flap 16 may be removed from the aperture with the flap, emptying the space defined by the aperture. However, unlike as outlined above the space within the aperture 12 would not be exposed, before the chad is removed.

Figure 3:
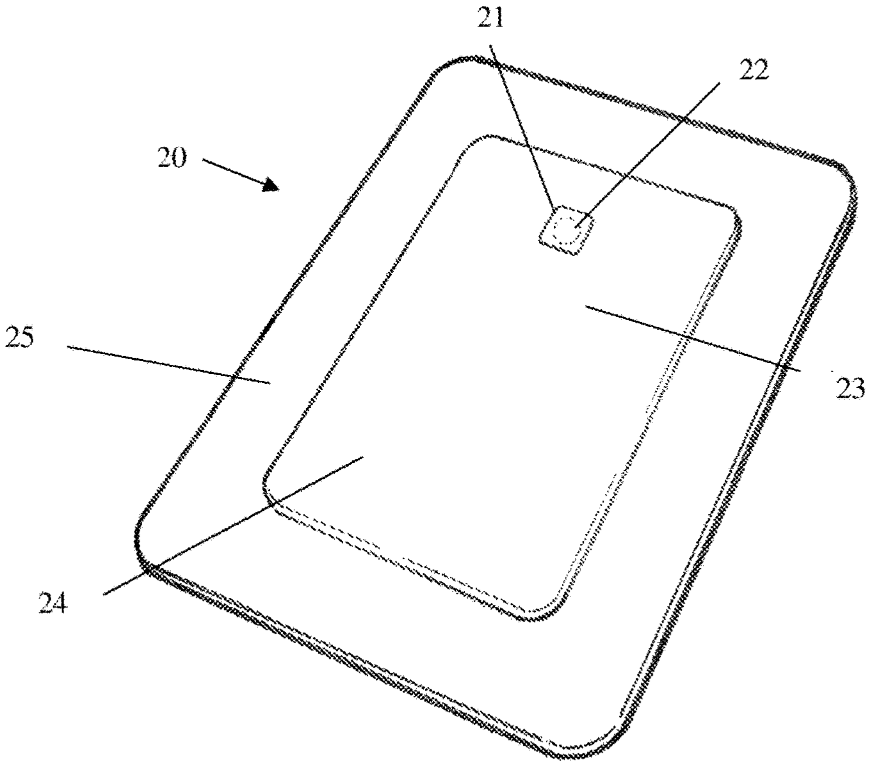
FIG. 3 is a schematic representation of another embodiment of a wound dressing configured for use without a wound therapy apparatus.

FIG. 3 illustrates a further embodiment of a wound dressing 20 in accordance with the invention.

As shown in FIG. 3, the wound dressing 20 includes an aperture 22 in a covering layer 23 of the dressing 20. The covering layer 23 has a raised central region 24, where it overlies a dressing body, which can include a pressure dispersion layer; an absorbent/superabsorbent layer/layers; and a wound-contact layer. The dressing 20 also has a border region 25, where it overlies an adhesive layer. A removable release layer (not shown) is provided on the underside.

The aperture 22 is covered with a semipermeable membrane 21, in this embodiment the semipermeable membrane 21 is provided on the exterior surface of the covering layer, however it will be evident to those skilled in the art that it equally could be applied to the interior surface of the covering layer. The semipermeable membrane of this embodiment is a polyurethane film of 25-30 microns in thickness, which is permeable to gas and moisture vapour, but impermeable to liquid and microbes. It may, for example have a moisture vapour transmission rate of 4500 $g/m^2/24$ hr Those skilled in the art will appreciate that a variety of materials can be selected for the semi-permeable membrane; dependent on the exact properties required, for example the gas and moisture vapour permeability.

To use the wound dressing 20 without a pressure gradient wound therapy system, the release layer on the underside is simply removed and the dressing 20 applied in the same way as an ordinary wound dressing. It will be noted semipermeable membrane 21 functions here as a microbial barrier, and as such, again the entire raised region formed by the covering layer 23 and the semipermeable membrane 21 is closed so bacteria cannot enter the cavity within the wound dressing 20 bounded by the border region 25.

To use the wound dressing 20 with a pressure gradient wound therapy system a source of non-atmospheric, e.g. negative, pressure can be connected to the aperture 22 to aid the wound-healing process.

For example, a port (not shown in FIG. 3) can be adhered to the wound dressing 20, such that a conduit through the port is aligned with the aperture 26; the port can be connected via tubing (also not shown in FIG. 3) to a pump (also not shown in FIG. 3) producing negative pressure. If the negative pressure wound therapy is to be "canister-less", the pump will produce a negative pressure beneath the dressing by withdrawing gas through the semi-permeable membrane 21. To use the wound dressing 20 with a system including a cannister, the semi-permeable membrane 21 can be removed (or broken) to allow fluid to be withdrawn through the aperture 22.

Those skilled in the art will appreciate that the steps to configure the wound dressing 20 for use with a pressure gradient wound therapy system can be undertaken either prior to or after the wound dressing 20 has been applied to the wound (i.e. the wound dressing can be configured for use with a pressure gradient wound therapy system in-situ).

FIGS. 4 to 7 illustrate a further embodiment of a wound dressing 30 in accordance with the invention.

Figure 4:
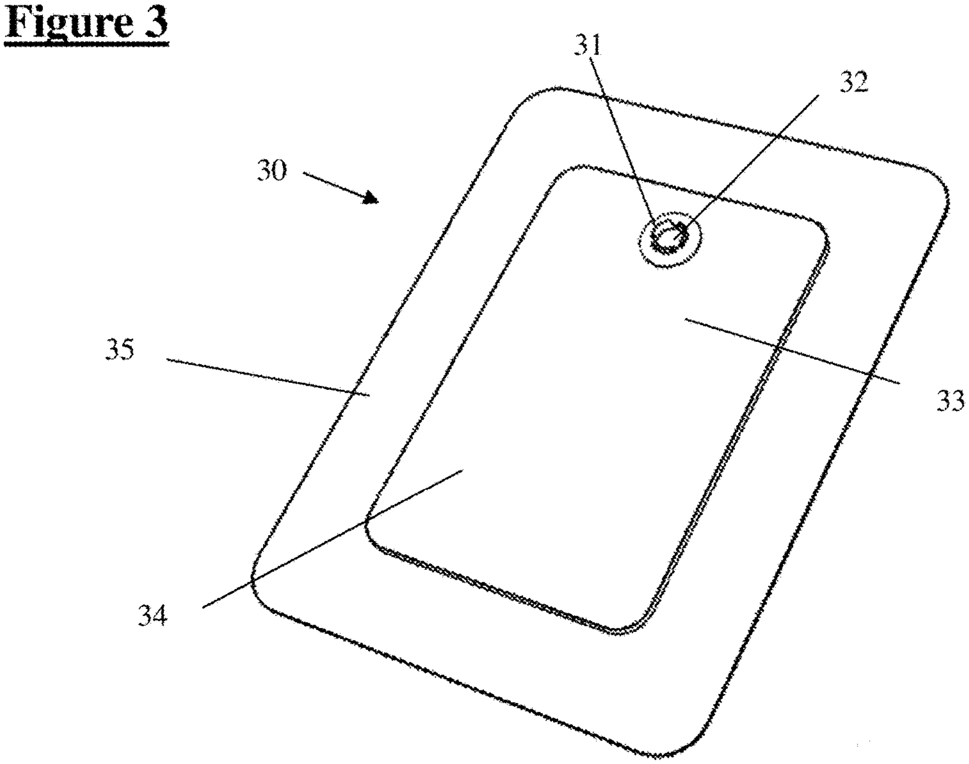
FIG. 4 is a schematic representation of another embodiment of a wound dressing configured for use without a wound therapy apparatus.

Referring to FIG. 4, the wound dressing 30 includes an aperture (not shown) in a covering layer 33 of the dressing 30. The covering layer 33 has a raised central region 34, where it overlies a dressing body, which can include a pressure dispersion layer; an absorbent/superabsorbent layer/layers; and a wound-contact layer. The dressing 30 also has a border region 35, where it overlies an adhesive layer. A removable release layer (not shown) is provided on the underside.

In this embodiment, the aperture is covered by a filter layer 32, which may, for example be a PTFE membrane filter, available from Whatman Plc® (alternative embodiments use a slimline cartridge or PTFE filter from Cole Parmer or a Gore-Tex® PTFE filter from W. L. Gore & Associates. As with the semi-permeable membrane of the previous exemplary embodiment, the filter 32 may be arranged on either an outer or inner surface of the covering layer 33, but in this embodiment the filter layer 32 is arranged on the underside of the connector base plate 31 which is disposed around the aperture, on the outer surface of the covering layer 33. A hole 36 in the centre of the base plate is aligned with the aperture in the covering layer 33.

Figure 6:
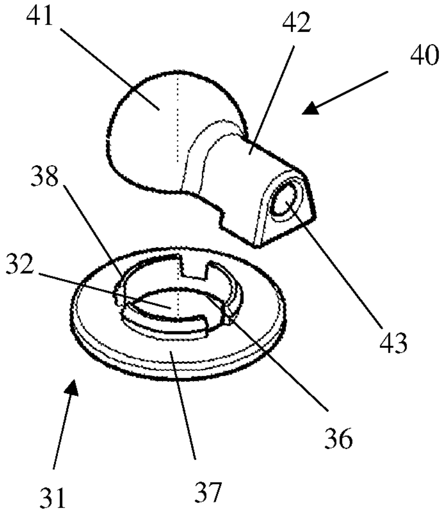
FIG. 6 is a schematic view of the unconnected port components of the wound dressing of FIG. 5.

FIG. 6 shows the connector base plate 31 and a second port component 40 in an unconnected configuration. The connector base plate 31 is an annular, low profile plate formed, for example, from flexible thermoplastics. The connector base plate has a lower surface (not shown) with the filter layer 32 thereon, which is adhered to the wound dressing 30. Opposite the lower surface is an upper surface 37, the upper surface comprises a means for connection to a second port component 40, in this case three projections 38 arranged on an inner edge of the upper surface 37, the three projections 38 projecting perpendicular to the upper surface 37. The projections 38 form a first part of a cantilever snap fitting between the connector base plate 31 and the second port component 40.

In this embodiment, the second port component 40 comprises a hemispherical body 41 and a tube connecting portion 42 projecting from the edge of the hemispherical body 41. A conduit is provided within the second port component 40 extending between a tube port 43 on the tube connecting portion 42 and a hole in the lower face of the second port component (not shown). Within the hole of the lower face a second part of the cantilever snap fitting is provided in the form of a recess configured to receive the projections of the first part of the cantilever snap fitting.

As illustrated in FIG. 4, to use the wound dressing 30 without a pressure gradient wound therapy system, the release layer on the underside is simply removed and the dressing 30 applied in the same way as an ordinary wound dressing. Again, it will be noted filter layer 32 functions here as a microbial barrier, and as such, again the entire raised region formed by the covering layer 33 and the filter membrane 32 is closed so bacteria cannot enter the cavity within the wound dressing 30 bounded by the border region 35.

Figure 5:
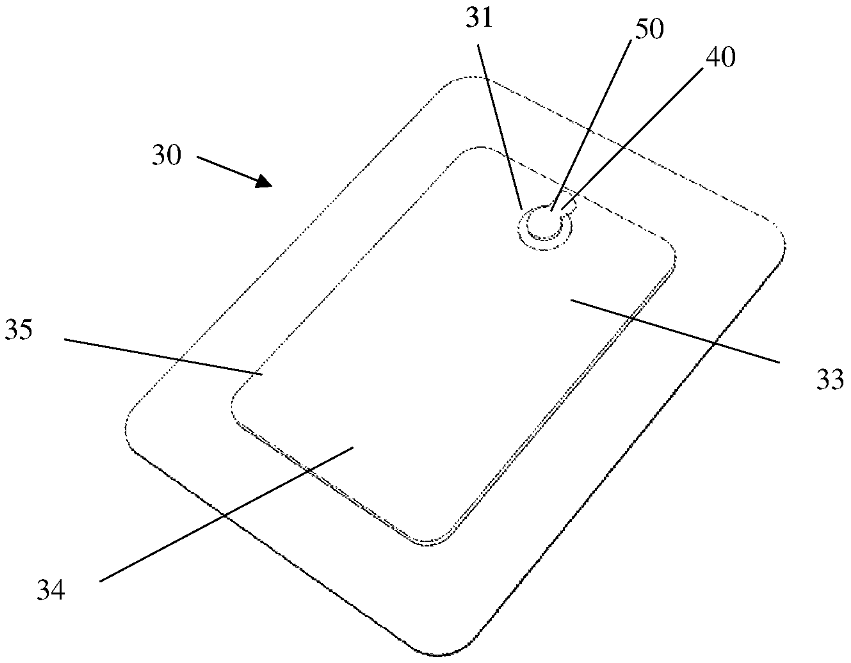
FIG. 5 is a schematic representation of the wound dressing of FIG. 4 configured for use with a wound therapy apparatus.
Figure 7:
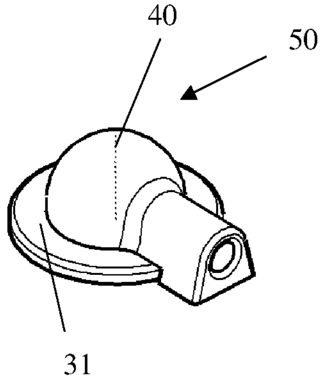
FIG. 7 is a schematic view of the connected port components of the wound dressing of FIG. 5.

FIG. 5 shows the wound dressing 30 configured for use with a pressure gradient wound therapy system. Here, a user has connected the second port component 40 to the port base plate 31 by means for the snap fitting forming a combined port 50 (that is, the combined port comprises the port base plate 31 and the second port component 40 as shown in FIG. 7). The combined port 50 is configured to connect to a source of non-atmospheric, e.g. negative, pressure which in turn allows the source of non-atmospheric pressure to be connected to the aperture to aid the wound-healing process.

The combined port 50 can be connected via tubing (not shown in FIG. 5) to a pump (also not shown in FIG. 5) producing negative pressure. If the negative pressure wound therapy is to be "canister-less", the pump will produce a negative pressure beneath the dressing by withdrawing gas through the filter membrane 32. To use the wound dressing 30 with a system including a cannister, the filter membrane 32 can be broken (e.g. cut) or removed to allow fluid to be withdrawn through the aperture.

Those skilled in the art will appreciate that the steps to configure the wound dressing 30 for use with a pressure gradient wound therapy system can be undertaken either prior to or after the wound dressing 30 has been applied to the wound (i.e. the wound dressing can be configured for use with a pressure gradient wound therapy system in-situ).

Figure 8:
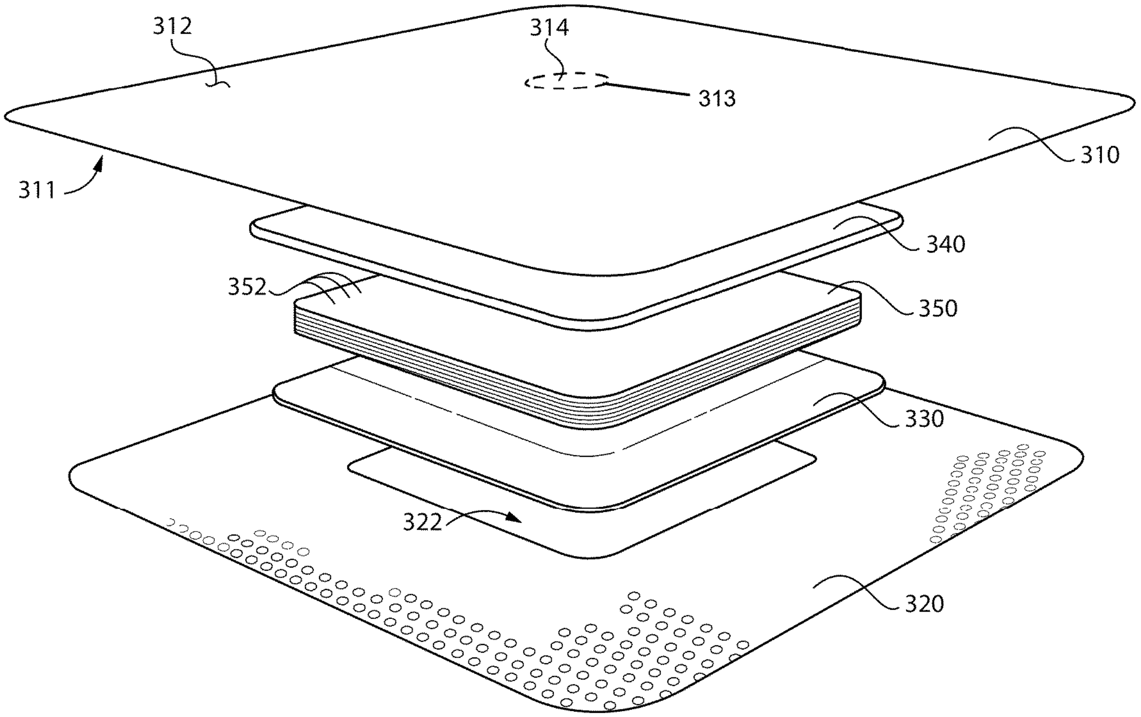
FIG. 8 is an exploded view of a wound dressing of any of FIGS. 1-5.
Figure 9:
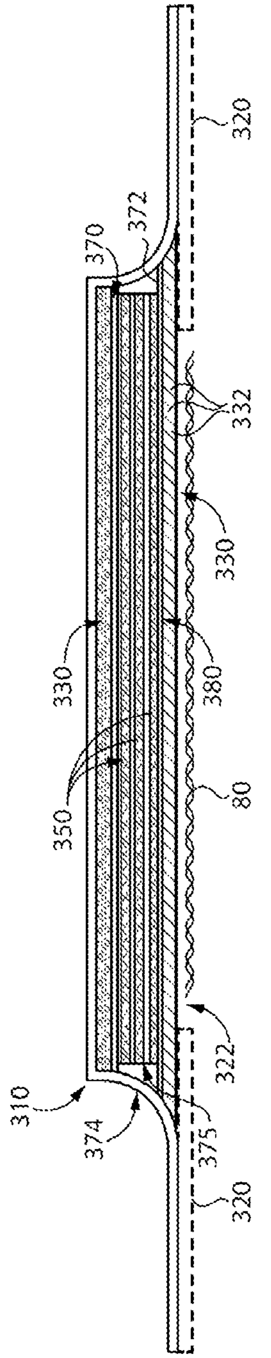
FIG. 9 is a cross sectional view through the wound dressing of FIG. 8.

With additional reference to FIGS. 8 and 9, illustrated therein is an exemplary layer composition of the wound dressings 10, 20, 30 of the above embodiments.

The illustrated wound dressing 300 generally includes a covering layer 310 and an adhesive layer 320 for adhering the wound dressing 300 adjacent the wound. In certain embodiments, the wound dressing 300 further comprises a wound contact layer 330 for contacting the wound, a pressure dispersion layer 340, a plurality of absorbent material layers 350 disposed between the wound contact layer 330 and the pressure dispersion layer 340.

The covering layer 310 has a first surface 311 and a second surface 312, and the first surface 311 is adjacent, and in contact with, the pressure dispersion layer 340 and the adhesive layer 320. The covering layer 310 defines a cavity in which the pressure dispersion layer 340 is arranged. In certain embodiments, the covering layer 310 is formed of a polyurethane film. The covering layer 310 comprises an aperture 314 is covered by a microbial barrier according to any of the previous embodiments.

The adhesive layer 320 generally defines a border about an opening 322 for receiving the wound. In certain embodiments, the adhesive layer 320 comprises a silicone adhesive. In certain embodiments, the adhesive layer 320 may be perforated.

The wound contact layer 330 overlaps the border defined by the adhesive layer 320, and is configured to contact the wound via the opening 322. In certain embodiments, the wound contact layer 330 may comprise Medicel™. In certain embodiments, the wound contact layer 330 comprises carboxymethylated cellulose fibers. In certain embodiments, the wound contact layer 330 may comprise HYDROFIBER®. In certain embodiments, the wound contact layer 330 may be reinforced, for example via nylon stitching. Thus, the wound contact layer 330 may comprise reinforcing nylon stitching 332.

The pressure dispersion layer 340 is adjacent and in contact with the first surface 311 of the cover layer 310. In certain embodiments, the pressure dispersion layer 340 may be provided as a polyester foam layer. In certain embodiments, the pressure dispersion layer 340 comprises reticulated foam.

The absorbent material layers 350 are positioned between the wound contact layer 330 and the pressure dispersion layer 340. The wound dressing 300 may, for example, comprise eight absorbent material layers 350. In certain embodiments, one or more of the absorbent material layers 350 may comprise carboxymethylated cellulose fibers. In certain embodiments, one or more of the absorbent material layers 350 may comprise Medicel™. In certain embodiments, one or more of the absorbent material layers 350 may comprise HYDROFIBER®. In certain embodiments, one or more of the absorbent material layers 350 further comprises fenestrations 352.

In certain embodiments, as shown in FIG. 9, the wound dressing 300 may include an additional layer 370 between the pressure dispersion layer 330 and the uppermost absorbent layer 350. The additional layer 370 may, for example, be formed of thermoplastic. In certain embodiments, the additional layer 370 may be provided as a thermoplastic spun lace layer. In certain embodiments, the wound dressing 300 may further comprise a nonwoven spun lace layer 372 connected to the wound contact layer 330. In certain embodiments, an envelope structure 374 is formed by joining peripheral portions 373 of the thermoplastic spun lace layer 370 and the nonwoven spun lace layer 372 such that the plurality of absorbent material layers 350 are disposed substantially within an interior cavity 375 of the envelope structure 374, for example as illustrated in FIG. 5. In certain embodiments, the absorbent material layers 350 are disposed within the interior cavity 375 of the envelope structure 374.

In certain embodiments, the wound dressing 300 may include a further layer 380 positioned between the wound contact layer 330 and the lowermost absorbent layer 350. The further layer 380 may, for example, be a polyester/viscose layer.

As is well known, and therefore not shown, the wound dressing 300 may be provided with a removable release layer on the underside, covering the adhesive layer 320 and the underside of the wound contact layer 330; and it may be individually packaged within a sterile package.

Figure 10:
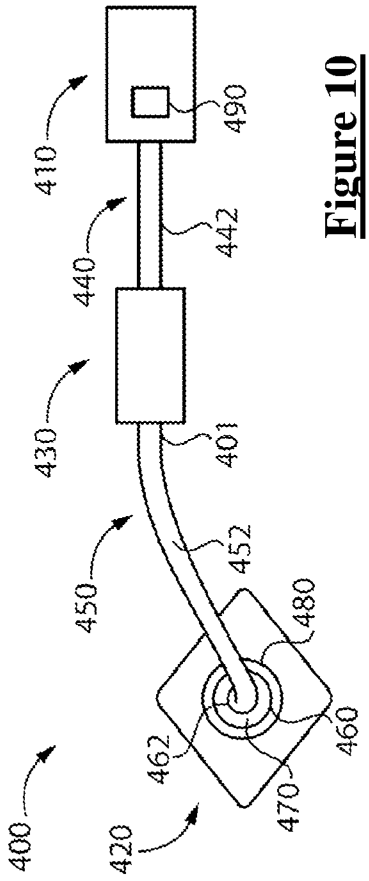
FIG. 10 is a schematic representation of a wound exudate management system according to certain embodiments.

With additional reference to FIG. 10, illustrated therein is a pressure gradient wound therapy system 400 according to certain embodiments. The pressure gradient wound therapy system 400 comprises a pump 410 for generating negative pressure, a wound dressing 420 (which may be any of the wound dressings 10, 20, 30, 300 described above) for covering and protecting a wound, an inline filter 430, a first pressure tube 440 having a first interior lumen 442, a second pressure tube 450 having a second interior lumen 452, and a flexible connector 460. The first pressure tube 440 is disposed between the pump 410 and the inline filter 430. The second pressure tube 450 is disposed between the inline filter 430 and the flexible connector 460. The flexible connector 460 is disposed between the second pressure tube 450 and the wound dressing 420 such that the pump 410 and the wound dressing 420 are in fluid communication via the interior lumens 442, 452.

Figure 11:
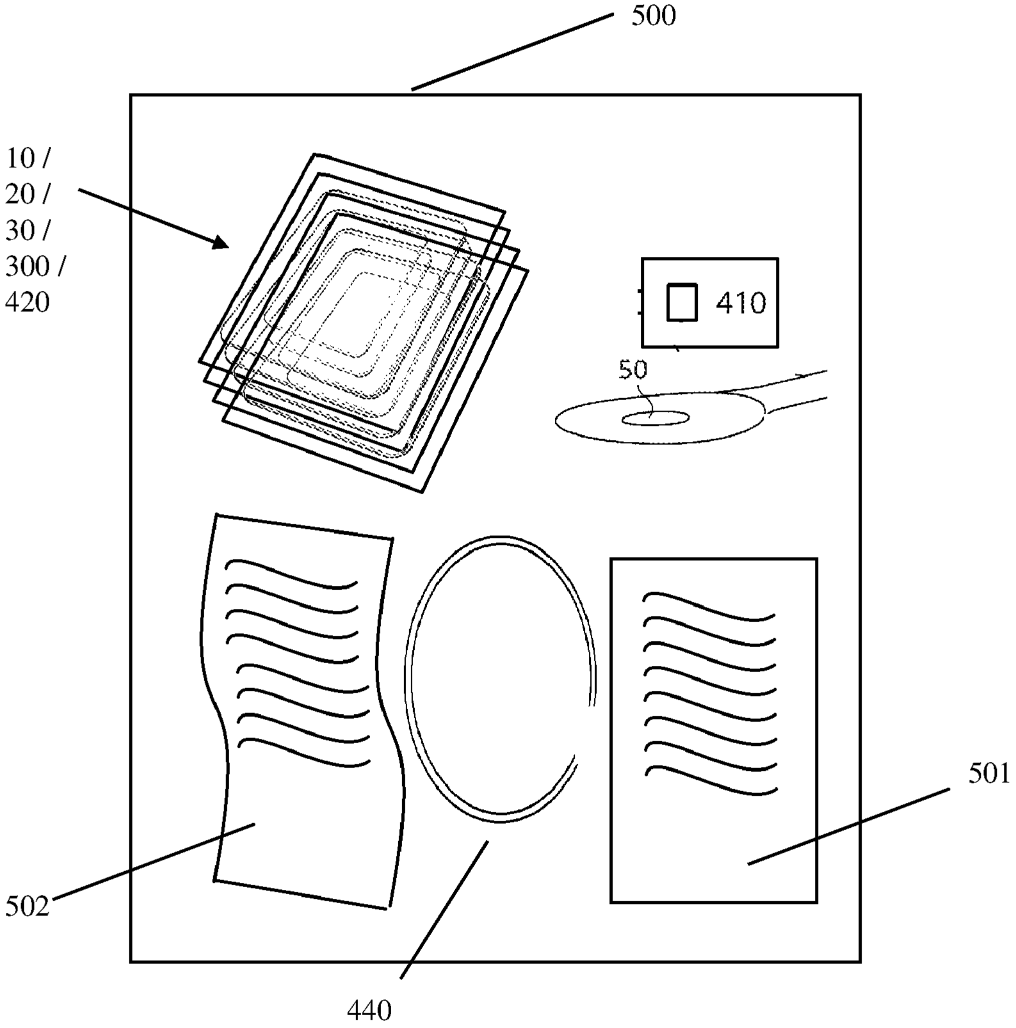
FIG. 11 is a schematic representation of a kit of parts.

The wound dressings 10, 20, 30, 300, 420 may be provided in kits. As illustrated schematically in FIG. 11, the kits can comprise one or preferably more than one of the selectively configurable wound dressings 10, 20, 30, 300, 420 and at least one of the following items, all of which are included in this exemplary kit:

(a) packaging 500 indicating that the wound dressing is selectively configurable for use in a pressure gradient wound therapy system and without a pressure gradient wound therapy system. In this example the packaging is a cardboard box, printed with instructions for use.

(b) instructions instructing a user as to how to configure the wound dressing for use in a pressure gradient wound therapy system and for use without a pressure gradient wound therapy system. In this example, the instructions are printed on a leaflet 502 included in the box.

(c) a source of non-atmospheric pressure. In this embodiment, the source of non-atmospheric pressure is the pump 410.

(d) a port for connection to the covering layer of the wound dressing to connect the wound dressing to a source of non-atmospheric pressure. In this embodiment the port is the port 50 described above.

(e) tubing for connection between a wound dressing and a source of non-atmospheric pressure. In this embodiment tubing 440 described above is included.

For use where it is envisioned that a wound will initially require treatment with a pressure gradient wound therapy system, the kit may comprise one or more, preferably a plurality of, dressings 10/20/30/300/420 and one or more of items c, d and e, for example all of items c, d, and e, and optionally items a and/or b as well. As such, the user can be provided with all the equipment required to use the wound dressings 10/20/30/300/420 with a pressure gradient wound therapy system.

In order to use such a kit, the user (e.g. a patient or HCP) can remove the flap 16 to expose the aperture; if using the dressings 10 of the first embodiment, in which the microbial layer is occlusive, attach a port 50 to the dressing, around the aperture, (or complete the port 50, if using the dressings 30 of the third embodiment); attach one end of the tubing 440 to the port 50 and the other to the pump 410 and run the pump 440 to provide non-atmospheric (e.g. negative) pressure to the wound.

Then, if/when the pressure gradient therapy is no longer necessary, the user can use up any remaining wound dressings 10/20/30/300/420 without the pressure gradient wound therapy system, by applying them to the wound without the elements of the pressure gradient wound therapy system and if using the dressings 10 of the first embodiment, without removing the microbial barrier, so as to maintain a sealed environment around the wound.

On the other hand, for use where it is envisioned that a wound does not require treatment with a pressure gradient wound therapy system (and most preferably where it is envisioned that a wound does not require treatment with a pressure gradient wound therapy system, but it is considered that there is a risk that the wound will not heal well without a pressure gradient so in future, pressure gradient wound therapy might be useful), the kit may comprise one, or more preferably a plurality of selectively configurable dressings 10/20/30/300/420 and one or both of items a and b. As such, the user has instructions on how to use the dressings without a pressure gradient wound therapy system and can simply apply a dressing 10/20/30/300/420 to the wound in the configuration for use without a pressure gradient wound therapy system. That is, remove the release layer on the underside and apply the wound dressing to the wound, so that the cover layer and microbial barrier form a closed cavity within the adhesive border, and the is wound sealed against bacteria/microbes.

Then, should it be determined that the wound would benefit from pressure gradient therapy (e.g. negative pressure), the user can follow the instructions from the packaging/instructions to configure the wound dressing 10/20/30 in-situ, that is, where applicable break the microbial barrier (e.g. remove the flap 16), then apply a port or second port component 40 and apply a source of non-atmospheric pressure as outlined above, without having first to remove the dressing 10/20/30/420 (which can present an opportunity for infection).

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Each of the documents referred to above is incorporated herein by reference. Except in Examples, or where otherwise explicitly indicated, all numerical quantities in this description specifying amounts of materials, device dimension, and the like, are to be understood as modified by the word "about."

Unless otherwise indicated, each chemical or composition referred to herein should be interpreted as being a commercial grade material which may contain the isomers, byproducts, derivatives, and other such materials which are normally understood to be present in the commercial grade.

The one or more embodiments are described above by way of example only. Many variations are possible without departing from the scope of protection afforded by the appended claims.

The invention claimed is:

1. A wound dressing selectively configurable for use in a pressure gradient wound therapy system and for use without the pressure gradient wound therapy system, the wound dressing comprising:

a wound contact layer having a first surface for contacting a wound and an opposing second surface;

a covering layer having a first surface facing the wound contact layer and defining a wound dressing cavity and an opposing second surface, the covering layer further comprising an aperture configured to provide fluid communication between the wound dressing cavity and an environment external to the wound dressing for use of the wound dressing with the pressure gradient wound therapy system; and an optionally removable or pierceable microbial barrier covering the aperture for use of the wound dressing without the pressure gradient wound therapy system and being configured for removal or piercing for use of the wound dressing with the pressure gradient wound therapy system, wherein the optionally removable or pierceable microbial barrier comprises a releasable layer, and wherein the covering layer comprises a plurality of perforations defining a perimeter of the aperture, wherein a section of the covering layer within the plurality of perforations is a removeable portion adhered to the releasable layer and configured to tear away from the covering layer.

2. A wound dressing according to claim 1, wherein the releasable layer is a flap, the flap comprising a covering portion and a release tab; wherein the covering portion is releasably adhered to the covering layer with a releasable adhesive and the release tab is not adhered to the covering layer.

3. A wound dressing according to claim 2 wherein the releasable adhesive is arranged on the second surface of the covering layer.

4. A wound dressing according to claim 3 wherein the release tab is configured to be pulled by a user to expose the aperture.

5. A wound dressing according to claim 4 wherein the releasable adhesive is configured to adhere to a port once the aperture is exposed.

6. A wound dressing according to claim 4, wherein when configured for use without the pressure gradient wound therapy system the wound dressing does not comprise a port.

7. A wound dressing according to claim 4, wherein the aperture is configured to provide fluid communication between the wound dressing cavity and a source of non-atmospheric pressure.

8. A wound dressing according to claim 1 wherein the microbial barrier comprises an occlusive material.

9. A wound dressing according to claim 8, wherein the microbial barrier is a foil.

10. A wound dressing according to claim 8, wherein the microbial barrier is a film.

* * * * *